US 11,819,216 B2

(12) United States Patent
Chen

(10) Patent No.: US 11,819,216 B2
(45) Date of Patent: Nov. 21, 2023

(54) EMBOLIC DEVICES FOR OCCLUDING BODY LUMENS

(71) Applicants: STRYKER CORPORATION, Kalamazoo, MI (US); STRYKER EUROPEAN OPERATIONS LIMITED, Carrigtwohill (IE)

(72) Inventor: Hancun Chen, San Ramon, CA (US)

(73) Assignees: STRYKER CORPORATION, Kalamazoo, MI (US); STRYKER EUROPEAN OPERATIONS LIMITED, Carrigtwohill (IE)

( * ) Notice: Subject to any disclaimer, the term of this patent is extended or adjusted under 35 U.S.C. 154(b) by 265 days.

(21) Appl. No.: 16/679,646

(22) Filed: Nov. 11, 2019

(65) Prior Publication Data

US 2021/0137529 A1  May 13, 2021

(51) Int. Cl.
*A61B 17/12* (2006.01)
*A61B 17/00* (2006.01)

(52) U.S. Cl.
CPC .. *A61B 17/12145* (2013.01); *A61B 17/12113* (2013.01); *A61B 2017/00323* (2013.01); *A61B 2017/00867* (2013.01)

(58) Field of Classification Search
CPC ........ A61B 17/12145; A61B 17/12113; A61B 17/1214; A61B 2017/00867; A61B 17/12131; A61B 17/12172
See application file for complete search history.

(56) References Cited

U.S. PATENT DOCUMENTS

| 9,023,094 B2 | 5/2015 | Tieu et al. |
| 2005/0079196 A1* | 4/2005 | Henkes ............ A61B 17/12022 424/423 |
| 2005/0187564 A1* | 8/2005 | Jayaraman ....... A61B 17/12022 606/141 |
| 2006/0206140 A1* | 9/2006 | Shaolian ............ A61B 17/1215 606/200 |
| 2009/0216263 A1 | 8/2009 | Tekulve |

FOREIGN PATENT DOCUMENTS

WO   WO 2013/142756   9/2013

OTHER PUBLICATIONS

PCT International Search Report and Written Opinion for International Appln. No. PCT/US2020/059499, Applicant Stryker Corporation, dated Feb. 18, 2021 (12 pages).

* cited by examiner

*Primary Examiner* — Diane D Yabut
*Assistant Examiner* — Christina C Lauer
(74) *Attorney, Agent, or Firm* — Vista IP Law Group, LLP

(57) ABSTRACT

An embolic device for placement in a body lumen, includes: an elongated member having a linear configuration when in room temperature, the elongated member being configured to form a first three-dimensional structure in response to body temperature; wherein the elongated member comprises a first segment, a second segment, and a third segment, the second segment being located between the first segment and the third segment; wherein the first segment and the third segment are configured to change their respective shapes in response to the body temperature; and wherein the second segment that is located between the first segment and the third segment has a shape that is independent of the body temperature.

16 Claims, 6 Drawing Sheets

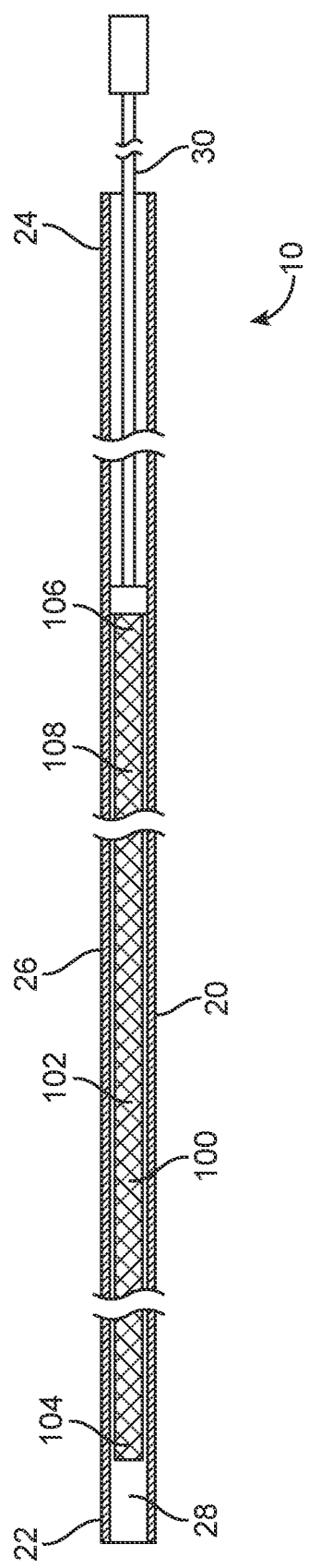
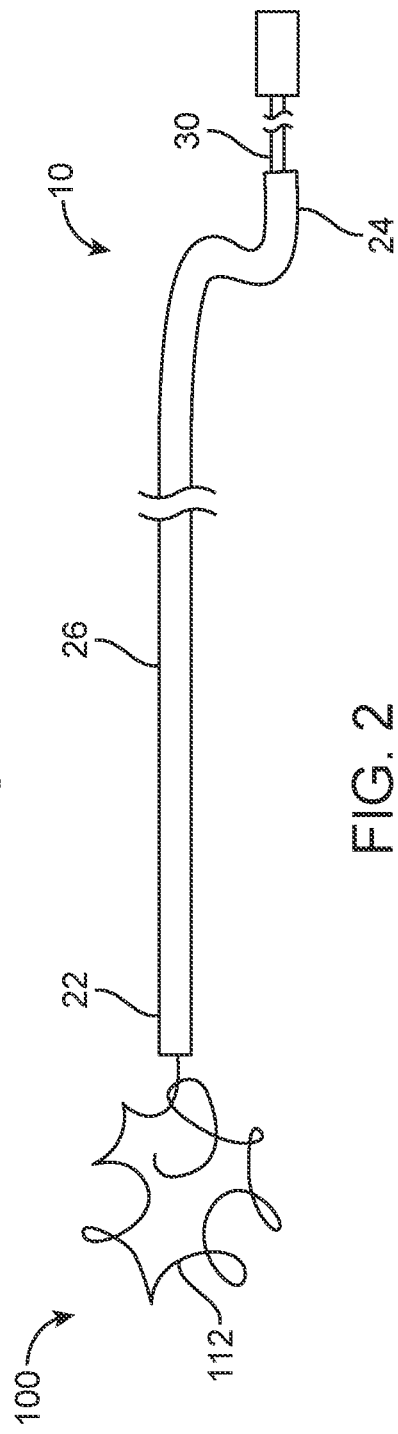
FIG. 1
FIG. 2

EMBOLIC DEVICES FOR OCCLUDING BODY LUMENS

FIELD

The field of the disclosure relates to medical devices and methods for occluding body lumens, and more specifically, to medical devices and methods for occluding aneurysms.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus, or to form such an embolus within an aneurysm stemming from the vessel.

Sometimes, when a vaso-occlusion device is being carried within the catheter, the vaso-occlusion device is elastically bent to conform with a profile of the catheter. This elastic bending of the vaso-occlusion device creates various pressure points against the inner surface of the catheter, which may be undesirable because it makes advancement of the vaso-occlusion device relative to the catheter harder. In some cases, increased axial force may need to be exerted in order to push the vaso-occlusion device distally. This increased axial force may sometimes cause premature buckling of the vaso-occlusion device inside the catheter.

Also, a vaso-occlusion device may assume a certain three-dimensional shape after it is deployed outside the catheter. If the deployed vaso-occlusion device is too stiff, it may not conform with a shape of the body cavity intended to be occluded by the vaso-occlusion device. On the other hand, if the deployed vaso-occlusion device is too flexible, then the vaso-occlusion device may not retain its shape, and may be unintentionally bent into an undesirable shape, rendering it incapable of occluding the body cavity.

New embolic devices for occluding body lumens that address the above problems would be desirable.

SUMMARY

An embolic device for placement in a body lumen, includes: an elongated member having a linear configuration when in room temperature, the elongated member being configured to form a first three-dimensional structure in response to body temperature; wherein the elongated member comprises a first segment, a second segment, and a third segment, the second segment being located between the first segment and the third segment; wherein the first segment and the third segment are configured to change their respective shapes in response to the body temperature; and wherein the second segment that is located between the first segment and the third segment has a shape that is independent of the body temperature.

Optionally, the first segment is configured to form a first part of a loop, and the third segment is configured to form a second part of the loop in response to the body temperature.

Optionally, the first segment is configured to form a first loop, and the third segment is configured to form a second loop, in response to the body temperature.

Optionally, the first segment has a first length, the second segment has a second length, and the third segment has a third length; and wherein the second length of the second segment is shorter than the first length of the first segment, and is also shorter than the third length of the third segment.

Optionally, the second length of the second segment that is between the first segment and the third segment is less than 50% of the first length of the first segment, and is also less than 50% of the third length of the third segment.

Optionally, the elongated member has a distal end and a proximal end opposite from the distal end, and wherein the embolic device further comprises a fourth segment that includes the proximal end; and wherein the fourth segment is martensitic when the fourth segment is in the room temperature, and is also martensitic when the fourth segment is in the body temperature.

Optionally, the first segment is martensitic when the first segment is in the room temperature, and is austenitic when the first segment is in the body temperature.

Optionally, the second segment is martensitic when the second segment is the room temperature, and is martensitic when the second segment is in the body temperature.

Optionally, the three-dimensional structure comprises a plurality of loops, and wherein the first segment, the second segment, and the third segment are parts of one of the loops.

Optionally, the elongated member further comprises a fourth segment, a fifth segment, and a sixth segment that are parts of another one of the loops; wherein the fifth segment is between the fourth segment and the sixth segment; wherein the fourth segment and the sixth segment are configured to change their respective shapes in response to the body temperature; and wherein the fifth segment that is located between the fourth segment and the sixth segment has a shape that is independent of the body temperature.

An embolic device for placement in a body lumen, includes: an elongated member having a linear configuration when in room temperature, the elongated member being configured to form a first three-dimensional structure in response to body temperature; wherein the elongated member comprises a first segment, a second segment, and a third segment, the second segment being located between the first segment and the third segment; wherein the first segment is martensitic when the first segment is in the room temperature, and is austenitic when the first segment is in the body temperature; and wherein the second segment is martensitic when the second segment is in the room temperature, and is also martensitic when the second segment is in the body temperature.

Optionally, the first segment is configured to form a first part of a loop, and the third segment is configured to form a second part of the loop, in response to the body temperature.

Optionally, the first segment is configured to form a first loop, and the third segment is configured to form a second loop, in response to the body temperature.

Optionally, the first segment has a first length, the second segment has a second length, and the third segment has a third length; and wherein the second length of the second segment is shorter than the first length of the first segment, and is also shorter than the third length of the third segment.

Optionally, the second length of the second segment that is between the first segment and the third segment is less than 50% of the first length of the first segment, and is also less than 50% of the third length of the third segment.

Optionally, the elongated member has a distal end and a proximal end opposite from the distal end, and wherein the embolic device further comprises a fourth segment that includes the proximal end; and wherein the fourth segment is martensitic when in the room temperature, and is also martensitic when the fourth segment is the body temperature.

Optionally, the three-dimensional structure comprises a plurality of loops, and wherein the first segment, the second segment, and the third segment are parts of one of the loops.

Optionally, the elongated member further comprises a fourth segment, a fifth segment, and a sixth segment that are parts of another one of the loops; wherein the fifth segment is between the fourth segment and the sixth segment; wherein the fourth segment and the sixth segment are martensitic when the fourth segment and the sixth segment are in the room temperature, and are austenitic when the fourth segment and the sixth segment are in the body temperature; and wherein the fifth segment is martensitic when the fifth segment is in the room temperature, and is also martensitic when the fifth segment is in the body temperature.

A method of occluding a body lumen performed by an embolic device having an elongated member, the elongated member comprising a first segment, a second segment, and a third segment, wherein the second segment is between the first segment and the third segment, includes: undergoing a first shape change by the first segment of the elongated member in response to body temperature; undergoing a second shape change by the second segment of the elongated member in response to force; and undergoing a third shape change by the third segment of the elongated member in response to the body temperature.

Optionally, the first segment is martensitic when the first segment is in the room temperature, and is austenitic when the first segment is in the body temperature; and wherein the second segment is martensitic when the second segment is in the room temperature, and is also martensitic when the second segment is in the body temperature.

Optionally, the first segment forms a first part of a loop, and the third segment forms a second part of the loop, in response to the body temperature.

Optionally, the first segment forms a first loop, and the third segment forms a second loop, in response to the body temperature.

Optionally, the first segment has a first length, the second segment has a second length, and the third segment has a third length; and wherein the second length of the second segment is shorter than the first length of the first segment, and is also shorter than the third length of the third segment.

Optionally, the second length of the second segment that is between the first segment and the third segment is less than 50% of the first length of the first segment, and is also less than 50% of the third length of the third segment.

Optionally, the elongated member has a distal end and a proximal end opposite from the distal end, and wherein the embolic device further comprises a fourth segment that includes the proximal end; and wherein the fourth segment is martensitic when in the room temperature, and is also martensitic when the fourth segment is the body temperature.

Optionally, the three-dimensional structure comprises a plurality of loops, and wherein the first segment, the second segment, and the third segment are parts of one of the loops.

Optionally, the elongated member further comprises a fourth segment, a fifth segment, and a sixth segment that are parts of another one of the loops; wherein the fifth segment is between the fourth segment and the sixth segment; wherein the fourth segment and the sixth segment are martensitic when the fourth segment and the sixth segment are in the room temperature, and are austenitic when the fourth segment and the sixth segment are in the body temperature; and wherein the fifth segment is martensitic when the fifth segment is in the room temperature, and is also martensitic when the fifth segment is in the body temperature.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 1 illustrates a medical device having a catheter for delivering an embolic device.

FIG. 2 illustrates the medical device of FIG. 1, particularly showing a distal segment of the embolic device being delivered out of the catheter.

DETAILED DESCRIPTION

Figure 3:
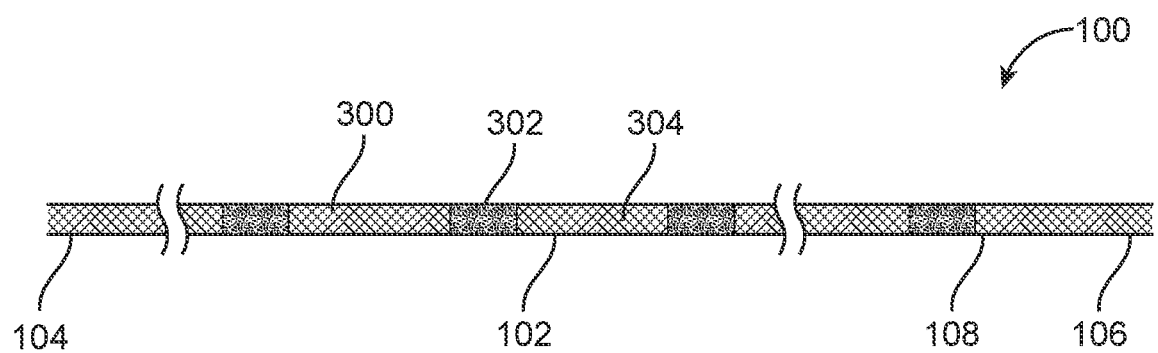
FIG. 3 illustrates an example of the medical device of FIG. 1, particular showing the device's shape when in room temperature.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a medical device 10 having a catheter 20 for delivering an embolic device 100 in a body lumen. The catheter 20 has a distal end 22, a proximal end 24, and a catheter body 26 extending between the distal end 22 and the proximal end 24. The embolic device 100 is contained within a lumen 28 of the catheter 20. The medical device 10 further includes a shaft 30 located in the lumen 28 for pushing the embolic device 100 out of the lumen 28 of the catheter 20.

As shown in FIG. 1, the embolic device 100 is made from an elongated member 102 having a distal end 104, a proximal end 106, and a body 108 extending between the distal end 104 and the proximal end 106. The elongated member 102 of the embolic device 100 has a linear configuration (e.g., a straight profile) when being in room temperature inside the catheter 20. The elongated member 102 is configured to form a three-dimensional structure 112 in response to body temperature when the elongated member 102 is delivered outside the catheter 20 into a patient's body (FIG. 2).

FIG. 3 illustrates an example of the embolic device 100. As shown in the figure, the elongated member 102 of the embolic device 100 has a linear configuration that is relatively straight when in room temperature. The elongated member 102 is configured to form the three-dimensional structure in response to body temperature. The straight profile of the elongated member 102 in the catheter 20 is thus mainly due to the elongated member 102 being in room temperature, and it is not mainly due to any mechanical straightening caused by the catheter 20. This feature is advantageous because it reduces friction between the elongated member 102 and the inner wall of the catheter 20 so that the embolic device 100 can be easier advanced distally. This feature also allows a longer embolic device 100 to be delivered if needed.

In the illustrated embodiments, the elongated member 102 has a first segment 300, a second segment 302, and a third segment 304. The second segment 302 is located between the first segment 300 and the third segment 304. The first segment 300 and the third segment 304 are configured to change their respective shapes in response to the body temperature. The second segment 302 that is located between the first segment 300 and the third segment 304 has a shape that is independent of the body temperature.

It should be noted that the term "body temperature", as used in this specification, may refer to a range of temperature, such as a temperature range of 95 F to 107 F, or more preferably a temperature range of 96 F to 100 F, or more preferably a temperature range of 97 F to 99 F. Also, as used in this specification, the term "room temperature" may refer to any temperature that is different from the body temperature. For example, room temperature may be any temperature that is lower than body temperature. In some embodiments, the room temperature may be any temperature that is at least 10 F below the body temperature, or that is at least 20 F below the body temperature.

In the illustrated embodiments, the first segment 300 is martensitic when the first segment 300 is in the room temperature, and is austenitic when the first segment 300 is in the body temperature. The second segment 302 is martensitic when the second segment 302 is the room temperature, and is martensitic when the second segment 302 is in the body temperature. The third segment 304 is martensitic when the third segment 304 is in the room temperature, and is austenitic when the third segment 304 is in the body temperature. Accordingly, the first and third segments 300, 304 are reversible Martensite segments that allow the first and third segments 300, 304 to have a relatively straight profile when in room temperature, and that allow the first and third segments 300, 304 to change to Austenite segments in response to body temperature. On the other hand, the second segment 302 is an irreversible Martensite segment that allows the second segment 302 to have a relatively straight profile when in both room temperature and body temperature.

In the illustrated embodiments, the second segment 302 is softer than the first segment 300 and the third segment 304. This allows the second segment 302 to more easily bend in response to force compared to the first and third segments 300, 304.

It should be noted that as used in this specification, the term "straight" may be used to describe a delivery shape of the embolic device 100 that is rectilinear or curvilinear, as long as the delivery shape has a curvature that is smaller than a curvature of the embolic device 100 in its deployed shape.

Figure 4:
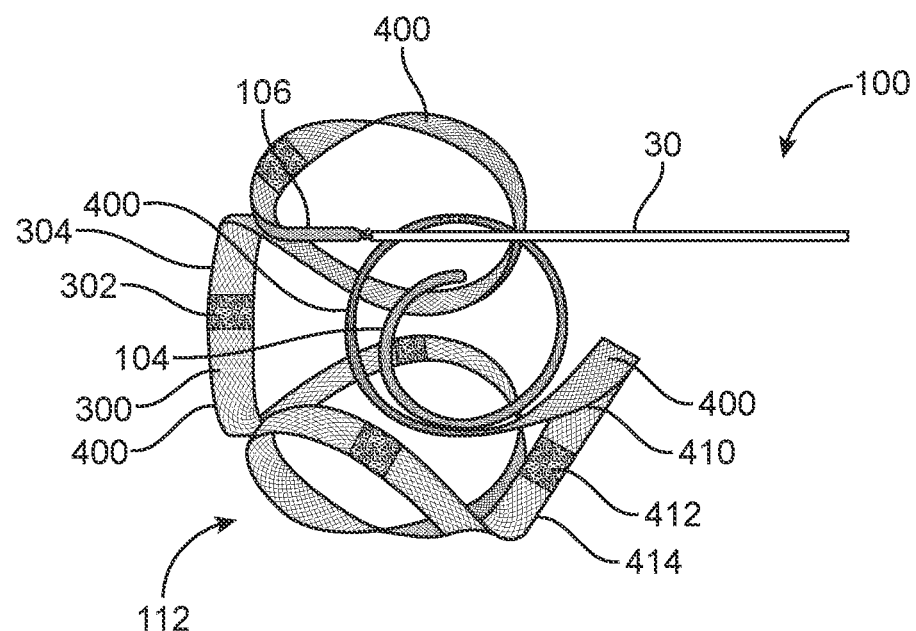
FIG. 4 illustrates the medical device of FIG. 3, particular showing the device's shape when in body temperature.

As shown in FIG. 4, the elongated member 102 is configured to form the three-dimensional structure 112 that comprises a plurality of loops 400 in response to body temperature after the elongated member 102 is deployed. As shown in the figure, the first segment 300, the second segment 302, and the third segment 304 are parts of one of the loops 400. Thus, the first segment 300 is configured to form a first part of a loop 400, and the third segment 304 is configured to form a second part of the same loop 400 in response to the body temperature.

As shown in the figure, the elongated member 102 further comprises a fourth segment 410, a fifth segment 412, and a sixth segment 414 that are parts of another one of the loops 400. The fifth segment 412 is between the fourth segment 410 and the sixth segment 414. The fourth segment 410 and the sixth segment 414 are configured to change their respective shapes in response to the body temperature. The fifth segment 412 that is located between the fourth segment 410 and the sixth segment 414 has a shape that is independent of the body temperature. In some embodiments, the fourth segment 410 and the sixth segment 414 are martensitic when the fourth segment 410 and the sixth segment 414 are in the room temperature, and are austenitic when the fourth segment 410 and the sixth segment 414 are in the body temperature; and wherein the fifth segment 412 is martensitic when the fifth segment 412 is in the room temperature, and is also martensitic when the fifth segment 412 is in the body temperature.

In some embodiments, the elongated member 102 may include multiple sets of three segments, with each set of the three segments being configured to form a loop (or other desired curvilinear shape) for the three-dimensional structure 112. In each set of the three segments, the first and the last segments are configured to change shape in response to body temperature, and the second segment that is between the first and the third segments has a shape that is independent of the body temperature. Thus, when the elongated member 102 is delivered from outside the patient to inside the patient, the elongated member 102 is subjected to a change in temperature from room temperature to body temperature. As a result, the first and third segments in each of the sets of the elongated member 102 will change their shapes in response to the body temperature, and the second segments in the sets of the elongated member 102 will not respond to the body temperature and will not changing their shapes due to the body temperature.

In some embodiments, the first segment 300 has a first length, the second segment 302 has a second length, and the third segment 304 has a third length. The second length of the second segment 302 is shorter than the first length of the first segment 300, and is also shorter than the third length of the third segment 304. For example, the second length of the second segment 203 that is between the first segment 300 and the third segment 304 may be less than 50% of the first length of the first segment, and is also less than 50% of the third length of the third segment.

In the above embodiments, the second segment 302 is described as being between the first segment 300 and the third segment 304, wherein all three segments 300, 302, 304 are parts of a loop. In other embodiments, the second segment 302 may be located at other positions. For example, in other embodiments, the second segment 302 may be located closer to one end of a loop. In such cases, the respective lengths of the first and third segments 300, 304 may be different from each other. As another example, in other embodiments, the second segment 302 may be located between two loops. In such cases, the first segment 300 is configured to form a first loop, and the third segment 304 is configured to form a second loop, in response to the body temperature. The second segment 302 located between the two loops (formed by the first and third segments 300, 304) does not change shape in response to the body temperature. Instead, the second segment 302 may be configured to change shape in response to force. In some cases, the second segment 302 may be located at an inflection point between two loops.

Also, in other embodiments, instead of having only one irreversible Martensite segment (e.g., segment 302) for each loop 400, the embolic device 100 may have multiple irreversible Martensite segments for each loop 400.

Figure 5:
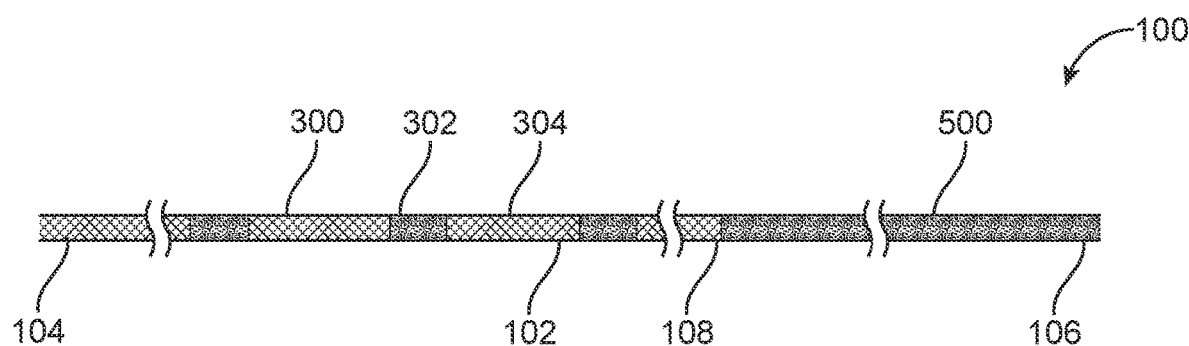
FIG. 5 illustrates another example of the medical device of FIG. 1, particular showing the device's shape when in room temperature.
Figure 6:
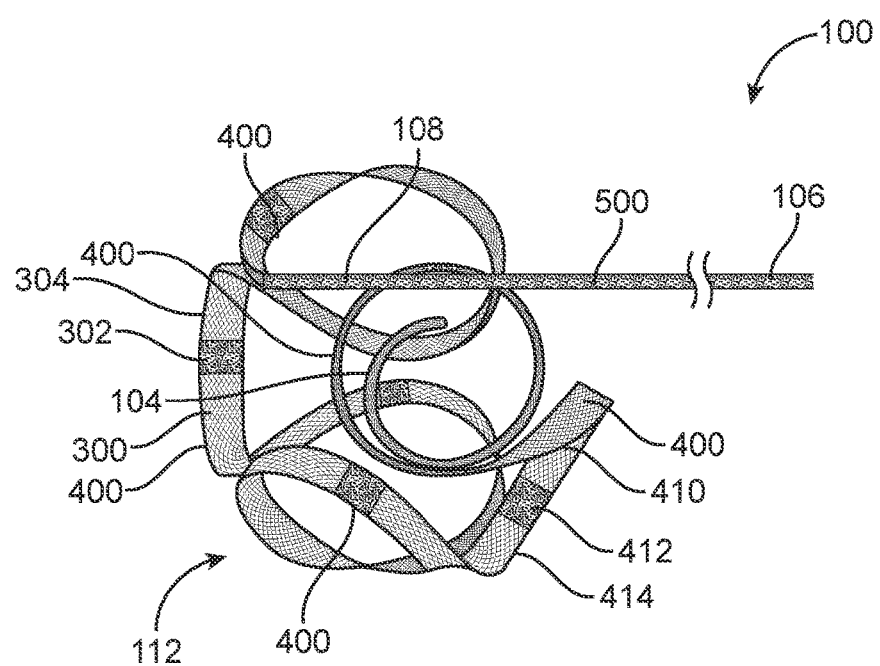
FIG. 6 illustrates the medical device of FIG. 5, particular showing the device's shape when in body temperature.

In one or more embodiments described herein, the embolic device 100 may optionally further include a segment at its proximal end. FIG. 5 illustrates another example of the embolic device 100. The embolic device 100 is similar to the embolic device 100 described with reference to FIGS. 3-4, except that the embolic device 100 further includes a segment 500 at its proximal end. As shown in FIG. 5, the embolic device 100 includes the first, second, and third segments 300, 302, 304 as similarly described. However, the embolic device 100 further includes a fourth segment 500 at the proximal end of the elongated member 102. The fourth segment 500 does not change shape in response to body temperature. As shown in FIG. 6, after the embolic device 100 is subjected to body temperature, a majority of the length of the elongated member 102 changes shape to form the three-dimensional structure 112. However, the fourth segment 500 remains straight and does not change its shape. Instead, the fourth segment 500 is configured to change shape in response to force. For example, when the embolic device 100 with the fourth segment 500 is delivered into an aneurysm, the interior wall of the aneurysm, or other parts of the embolic device 100 that have already been delivered inside the aneurysm, may exert a force on the fourth segment 500 when the fourth segment 500 is pushed out of the catheter 20. This will cause the fourth segment 500 to bend. In some embodiments, the fourth segment 500 is martensitic when the fourth segment is in the room temperature, and is also martensitic when the fourth segment 500 is in the body temperature. Also, in some embodiments, the fourth segment 500 is softer than a segment with shape-memory characteristic (e.g., first segment 300, third segment 302, etc.). Accordingly, the fourth segment 500 can bend easier when an external force is applied. This allows the fourth segment 500 to be formed into any shape, depending on a direction and magnitude of the external force. In some cases, the fourth segment 500 may be configured for filling purpose to fill a space inside a body cavity, such as an aneurysm. In some embodiments, the fourth segment 500 may have a length that is greater than a length of a preceding loop 400. For example, the fourth segment 500 may have a length that is equal to 1×, 2×, 3× or 4× the length of the segment forming a preceding loop 400.

In some embodiments, the fourth segment 500 may be made from the same material as that for segment 302, and may have the same mechanical property as that of segment 302. In other embodiments, the fourth segment 500 may be softer than the segment 302.

In the illustrated embodiments, the loops 400 of the three-dimensional structure 112 are connected by respective inflection points, which allow adjacent loops 400 to form reverse curvatures. In other embodiments, adjacent loops 400 of the three-dimensional structure 112 may not form reverse curvatures. Furthermore, in other embodiments, instead of loops, the first three-dimensional structure 112 may have other structural elements with shapes that are not loops.

In some embodiments, the curvatures of the loops 400 of the three-dimensional structure 112 may be the same. In other embodiments, one or more of the loops 400 may be different from another one of the loops 400 in the three-dimensional structure 112. For example, in some embodiments, the three-dimensional structure 112 may have a first loop 400 with a first curvature, and a second loop 400 proximal to the first loop 400, wherein the second loop 400 may have a second curvature that is higher than the first curvature of the first loop 400. In other embodiments, the three-dimensional structure 112 may have a first loop 400 with a first curvature, and a second loop 400 proximal to the first loop 400, wherein the second loop 400 may have a second curvature that is lower than the first curvature of the first loop 400. As used in this specification, "curvature" may be defined as 1/R, where R may be the smallest radius of curvature associated with the curve.

In some embodiments, the three-dimensional structure 112 has at least two loops 400 (e.g., at least two adjacent loops 400) with respective loop dimensions that do not vary by more than 10%, and preferably that do not vary by more than 5%. For example, in one implementation, the three-dimensional structure 112 may have loops 400 with the same loop dimension (e.g., loop width or diameter). In other embodiments, the three-dimensional structure 112 may have loops 400 with respective loop dimensions that vary by more than 10%.

In addition, in some embodiments, the loops 400 in the three-dimensional structure 112 have respective loop dimensions that reduce along the length of the elongated member 102 from the distal-to-proximal direction. This feature is advantageous because it assists the elongated member 102 in forming different filling structures that are smaller than the previous ones, thereby allowing the subsequent filling structures to fit within the previous ones.

In some embodiments, a first portion of the embolic device 100 may have a first width, and a second portion of the embolic device 100 that is proximal to the first portion may have a second width that is less than the first width. Alternatively or additionally, the first portion of the embolic device 100 may have a first thickness, and the second portion of the embolic device 100 may have a second thickness that is less than the first thickness. In one implementation, the elongated member 102 may be a braided structure, and the narrower width and/or thickness of the second portion of the embolic device 100 may be accomplished by using fewer strands of fiber to form the braid for the second portion compared to the number of strands of fiber used to form the braid for the first portion. Alternatively, the narrower width (or thickness) of the second portion of the embolic device 100 may be accomplished by cutting or grinding away (e.g., using laser cutter, grinder, etc.) some of the member that is used to form the second portion. As another alternative, the first and second portions of the embolic device 100 may be formed from separate members with different respective cross-sectional dimensions. In such cases, the members may be secured to each other, e.g., using adhesive, weld, fusion, mechanical coupler, etc. It should be noted that the terms "width" and "thickness" may refer to the longer and shorter dimensions of a cross section in some cases, such as cross section having a rectangular shape or an elliptical shape. However, use of either of these terms should not imply that the cross section has an elongated shape. For example, width or thickness of a cross section may refer to a cross sectional dimension of a circular cross section, a square cross section, a hexagon cross section, a pentagon cross section, etc.

Also, in some embodiments, the angles (between adjacent loops 400) of the three-dimensional structure 112 may progressively reduce in the distal-to-proximal direction along the length of the elongated member 102. This feature is advantageous because it may allow a distal portion of the elongated member 102 to form a first part of a three-dimensional structure 112 that is along a perimeter of a body cavity, and also may allow a proximal portion of the elongated member 102 to form a second part of the three-dimensional structure 112 that can fit within the first part of the three-dimensional structure 112. In one implementation, a first portion of the elongated member 102 may be configured to form a first plurality of loops 400 with a first plurality of angles between adjacent ones of the first plurality of loops 400, and a second portion of the elongated member 102 may be configured to form a second plurality of loops 400 with a second plurality of angles between adjacent ones of the second plurality of loops 400. The first plurality of angles may be the same as each other, and the second plurality of angles may be the same as each other. However, the first plurality of angles may be larger than the second plurality of angles.

As discussed, in some embodiments, the elongated member 102 may have progressively reducing angles between adjacent loops from distal end to proximal end of the elongated member 102. This allows the elongated member 102 to fill a body cavity from "outside-towards-inside" so that an outer space within the body cavity is filled first before the inner space in the aneurysm. In other embodiments, the elongated member 102 may have progressively increasing angles between adjacent loops from distal end to proximal end of the elongated member 102. This allows the elongated member 102 to fill the body cavity from "inside-towards-outside" so that an inner space within the body cavity is filled first before the outer space in the body cavity.

In some embodiments, the elongated member 102 of the embolic device 100 may be a braided structure. In one implementation, the elongated member 102 may be formed by twenty-four strands of fibers that are braided. Alternatively, other numbers of strands of fibers may be used to form the elongated member. Also, in some embodiments, a proximal portion of the elongated member 102 may be formed using more strands compared to a distal portion of the elongated member 102. In other embodiments, the distal portion of the elongated member 102 may be formed using more strands compared to the proximal portion of the elongated member 102, thereby making the distal portion stiffer compared to the proximal portion.

In other embodiments, the elongated member 102 of the embolic device 100 may be a coil. In such cases, the elongated member 102 has a primary shape that is a coil, and the coil may then be bent to form a desired secondary shape (deployed shape).

In further embodiments, the elongated member 102 of the embolic device 100 may be a solid continuous member. In such cases, the solid continuous member has a primary shape that is straight, and the solid continuous member may then be bent to form a desired secondary shape (deployed shape).

In one or more embodiments described herein, the length of the elongated member 102 of the embolic device 100 may be anywhere from 15 cm to 50 cm, or from 25 cm to 45 cm, or from 30 to 40 cm. In other embodiments, the length of the elongated member 102 of the embolic device 100 may be less than 15 cm or more than 40 cm.

Also, in one or more embodiments described herein, the elongated member 102 of the embolic device 100 may be made from any suitable materials. By means of non-limiting examples, the elongated member 102 of the embolic device 100 may be made from Nitinol®, AuPt, stainless steel, platinum, other metals, other alloys, or any combination of the foregoing.

In some embodiments, each previous portion of the elongated member 102 forms a filling structure that allows accommodation of later portion(s) of the elongated member 102. This allows different layers of structures to be progressively delivered into the aneurysm in a nesting configuration to fill the aneurysm from the periphery towards the center of the aneurysm. In some embodiments, a first portion of the elongated member 102 may have a first set of loops, a second portion of the elongated member 102 proximal to the first portion may have a second set of loops, a third portion of the elongated member 102 proximal to the second portion may have a third set of loops, etc. The first set of loops may have loop widths that are the same in size, or that decrease in size in the distal-to-proximal direction. Similarly, the second set of loops may have loop widths that are the same in size, or that decrease in size in the distal-to-proximal direction. Also, the third set of loops may have loop widths that are the same in size, or that decrease in size in the distal-to-proximal direction. In addition, in some embodiments, the first (i.e., distal) loop in a subsequent portion of the elongated member 102 may have a width that is smaller than a width of the last (i.e., proximal) loop in a previous portion of the elongated member 102. Alternatively, in other embodiments, the first (i.e., distal) loop in a subsequent portion of the elongated member 102 may have a width that is larger than a width of the last (i.e., proximal) loop in a previous portion of the elongated member 102.

In one or more embodiments described herein, the embolic device 100 may optionally further include a distal loop at the distal end of the embolic device 100, wherein the distal loop has a diameter that is 75% of less of the diameter of the loop proximal to the distal loop. As used in this specification, a "diameter" of a loop does not necessarily imply that the loop has a circular shape, and the term "diameter" may refer to a width of a loop, which may or may not be circular in shape. For example, a diameter of a loop may refer to a largest width of the loop in some cases.

Also, in one or more embodiments described herein, the embolic device 100 may optionally further include a distal coil at the distal end of the embolic device 100. In one implementation, if the elongated member 102 of the embolic device 100 is formed from a braid, the distal coil may be formed from one or more strands of the braid. In another implementation, a separate coil may be provided as the distal coil, and is then attached to the distal end of the elongated member 102.

In addition, in one or more embodiments described herein, the embolic device 100 may optionally further include a proximal coil at the proximal end of the embolic device 100. In one implementation, if the elongated member 102 of the embolic device 100 is formed from a braid, the proximal coil may be formed from one or more strands of the braid. In another implementation, a separate coil may be provided as the proximal coil, and is then attached to the proximal end of the elongated member 102. The proximal coil is advantageous because it may provide stiffness transition from the embolic device 100 to the shaft 30.

Also, in one or more embodiments described herein, a proximal portion of the embolic device 100 may have a stiffness (e.g., bending stiffness and/or axial stiffness) that is different from a stiffness (e.g., bending stiffness and/or axial stiffness) of a distal portion of the embolic device 100. In some embodiments, the proximal portion of the embolic device 100 may have a column strength that is different from a column strength of the distal portion. For example, the column strength of the proximal portion of the embolic device 100 may be higher than a column strength of the proximal portion of the embolic device 100. This is advantageous because it allows the embolic device 100 to be pushed distally inside the catheter 20 without buckling. The relative difference in column strength and/or stiffness may be achieved using metallurgical heat treat condition, by variation in the cross-sectional dimension, and/or by varying number of strands in a braided structure, along the length of the elongated member 102.

Also, in one or more embodiments described herein, if the elongated member 102 is a braided structure, the braid angle of the strands along the length of the member 102 may be varied in order to change the stiffness along the length of the elongated member 102. For example, in some embodiments, a proximal portion of the elongated member 102 and a distal portion of the elongated member 102 may have the same number of strands, but the braid angle (e.g., angle formed by the strands with respect to the longitudinal axis of the member 102) of the strands in the proximal portion may be larger than the braid angle of the strands in the distal portion, thereby making the proximal portion of the elongated member 102 stiffer than the distal portion of the elongated member 102. In other embodiments, the braid angle of the strands in the distal portion of the elongated member 102 may be larger than the braid angle of the strands in the proximal portion of the elongated member 102, thereby making the second portion of the elongated member 102 softer than the first portion of the elongated member 102. Also, in some embodiments, the braid angle of the strands along the length of the member 102 may vary gradually.

In addition, in some embodiments, the three-dimensional structure comprises a first plurality of loops 400, and wherein loop widths, loop curvatures, braid widths, braid angles, or any combination of the foregoing, of the respective ones of the first plurality of loops 400 increase or decrease along a length of the elongated member 102 forming the three-dimensional structure 112.

In addition, in some embodiments, the three-dimensional structure 112 comprises a plurality of loops 400, and wherein angles between adjacent ones of the plurality of loops 400 increase or decrease along a length of the elongated member 102 forming the three-dimensional structure 112.

Furthermore, it should be noted that the embolic device 100 is not limited to the examples described herein, and that the embolic device 100 may have other configurations in other embodiments. For example, in other embodiments, the embolic device 100 may be configured to form other three-dimensional structures that are different from the ones described herein.

In further embodiments, the embolic device 100 is not configured to fill a body cavity from the periphery of the body cavity towards the center, nor is it configured to fill the body cavity from the center towards the periphery of the body cavity. Instead, the embolic device may be configured to fill the body cavity from one side of the body cavity towards an opposite side. Alternatively, the embolic device may be configured to fill the body cavity in a random manner.

Various techniques may be used to form the embolic device 100. In some embodiments, the elongated member 102 may be wrapped around one or more mandrels to form a desired shape. The mandrel(s) may include multiple posts configured to allow the elongated member 102 to wrap there-around. The sizes of the posts will dictate the loop sizes of the loops to be formed. Also, the relative orientation of the posts will dictate the relative angles among the loops to be formed. After the elongated member 102 has been wrapped around the mandrel(s), the elongated member 102 may be chemically treated and/or heat treated to achieve the deployed shape of the elongated member 102, and/or to provide different mechanical properties for different portions of the elongated member 102.

In some embodiments, controlled heating and/or local heating may be performed so that the different segments along the length of the elongated member 102 will have different phase transition temperatures. This can be done for example by laser heating. In particular, a first heat treatment condition may be applied to a first set of segments (e.g., segment 302, 412, etc.) along the length of the elongated member 102, so that their transformation temperature is higher than body temperature (37C). Accordingly, these segments will retain their Martensite phase when the device is deployed into a treatment site. They are therefore considered to be irreversible Martensite segments since there is no phase transformation of Martensite into Austenite. In contrast, a second heat treatment condition may be applied to a second set of segments (e.g., segments 300, 304, 410, 414, etc.), so that their transformation temperature is lower than body temperature (37C). These segments will have a phase transformation from Martensite to Austenite when the embolic device 100 is deployed into the treatment site. They are considered to be reversible Martensite segments. In general, thermal induced Martensite occurs as twinned Martensite, and the twinned Martensite structures can turn into detwinned structures by deforming the material in the martensitic condition in response to the material reaching a transition temperature.

In other embodiments, deformation strain control may be applied to the different segments along the length of the elongated member 102. In particular, a first strain condition may be applied to a first set of segments (e.g., segments 302, 412, etc.) in such a way that the strain exceeds its recoverable limit of the Martensite phase, and therefore the Martensite phase cannot transfer to Austenite phase when the embolic device is deployed into the treatment site. These segments retain Martensite phase all the time, and therefore are considered to be irreversible Martensite segments. On the other hands, a second strain condition may be applied to a second set of segments (e.g., segments 300, 304, 410, 414, etc.) in such a way that the strain level is within their recoverable limit, and therefore the Martensite phase will transfer to Austenite phase when the embolic device 100 is deployed into the treatment site. These segments are therefore considered to be reversible Martensite segments.

In other embodiments, parts of the elongated member 102 may be covered by a shielding material while other parts of the elongated member 102 are chemically and/or heat treated. This allows different parts of the elongated member 102 to be formed having different mechanical properties. For example, this technique may be used to make irreversible Martensite segments and reversible Martensite segments along the length of the elongated member 102.

In further embodiments, a combination of the above techniques may be employed to create the irreversible Martensite segments and the reversible Martensite segments along the length of the elongated member 102.

Other techniques for shaping an elongated member may be used in other embodiments to form the embolic device 100.

Figure 7:
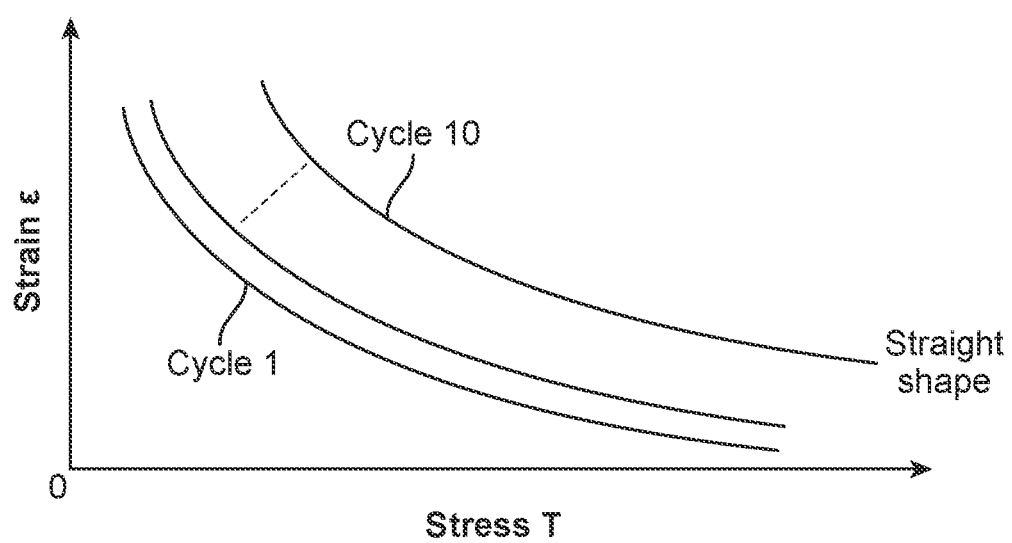
FIG. 7 is a stress-strain graph, particularly showing an effect of thermal cycling.

After the elongated member 102 has been formed to have the deployed shape (e.g., like the examples shown in FIG. 4 and FIG. 6), and to have both irreversible Martensite segments (e.g., segments 302, 412, etc.) and reversible Martensite segments (e.g., segments 300, 304, 410, 414, etc.) along the length of the elongated member 102, the elongated member 102 may be further treated to form a delivery shape (e.g., like the examples shown in FIG. 3 and FIG. 5). In some embodiments, such may be accomplished using thermal cycling. For example, the elongated member 102 (already formed to have the deployed shape) may be subject to repeated heating and cooling while the elongated member 102 is placed in a desired delivery shape to be formed. In one technique, the elongated member 102 may be tensioned into a straight profile while subjecting it to repeated heating and cooling. In some embodiments, the heating may be performed heat the elongated member 102 to a temperature that is higher than 80° C., or more preferably higher than 90° C. (e.g., 100° C.), or more preferably higher than 100° C. Also, in some embodiments, the cooling may be performed to cool the elongated member 102 to a temperature that is below 10° C., or more preferably below 0° C., or more preferably below −10° C. This technique can be employed to create the embolic device 100 so that it has a first shape (delivery shape) when it is in room temperature, and a second shape (deployed shape) when it is in body temperature, such as when the embolic device 100 is deployed inside the patient. FIG. 7 is a stress-strain graph, particularly showing an effect of thermal cycling. As can be seen from the graph, when the elongated member 102 is subjected to heating and cooling, thermal stress is applied to the elongated member 102, thereby shifting the stress-strain curve of the elongated member 102. If the heating and cooling is repeated for additional cycle(s), additional thermal stress is applied to the elongated member 102, thereby shifting the stress-strain curve further.

It should be noted that the transition temperature at which the embolic device 100 will change from the delivery shape to the deployed shape can be selectively configured using material composition and/or manufacturing process. For example, the Austenite finishing temperature may be selected for the manufacturing process for a certain given material so that the finished product will have a desired transition temperature.

Figure 8A:
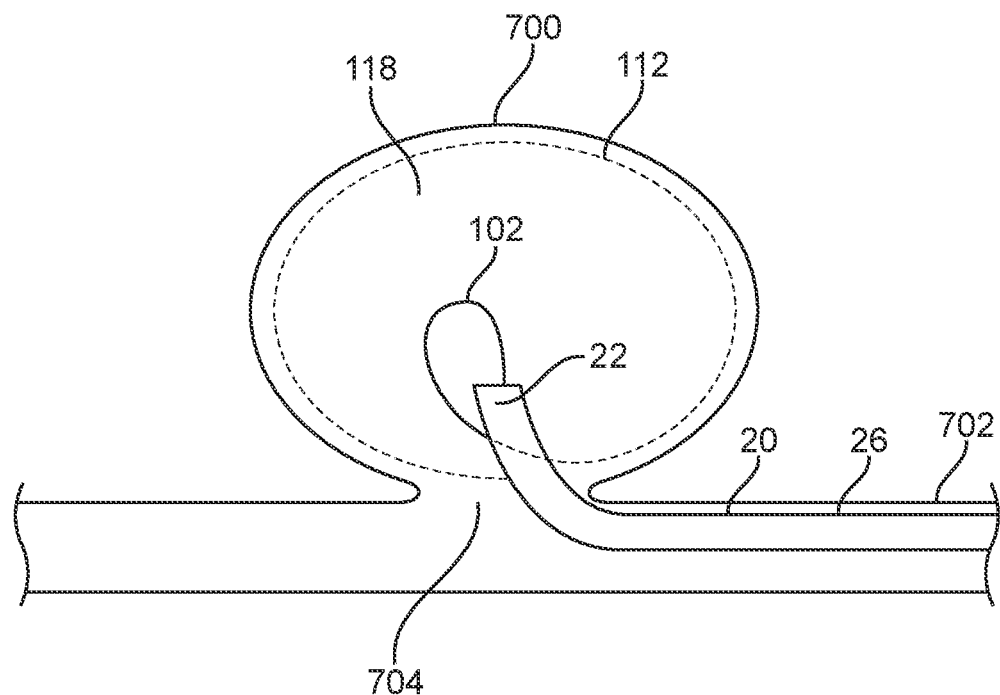
FIGS. 8A-8B illustrate a method of using the medical device of FIG. 1.
Figure 8B:
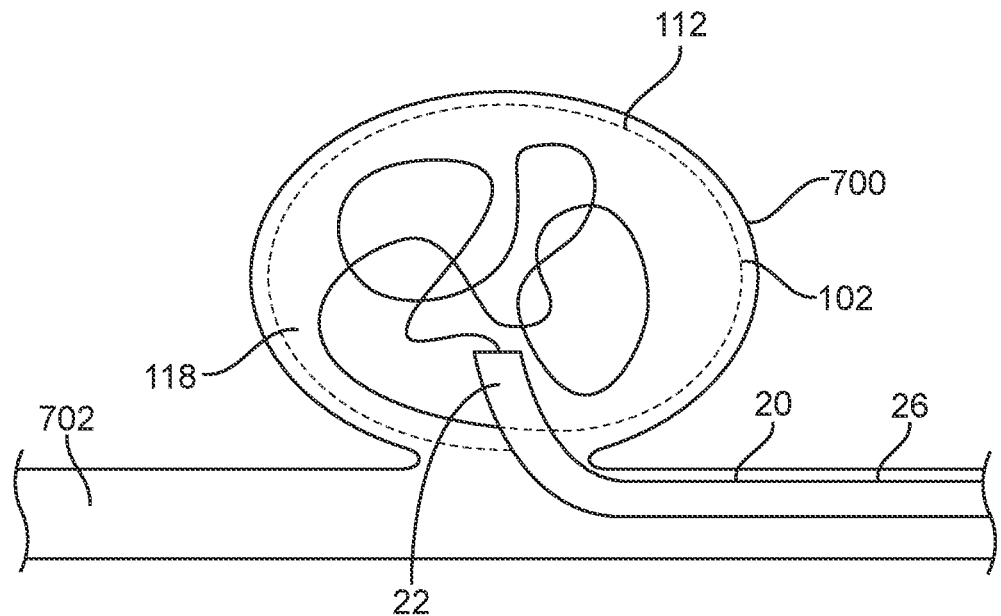

FIGS. 8A-8B illustrate a method of using the medical device 10 of FIG. 1 to treat an aneurysm 700. When using the medical device 10, the catheter 20 is first inserted into a blood vessel 702 of a patient through an incision. The catheter 20 is then advanced distally until the distal end 22 of the catheter 20 is at the aneurysm 700.

In some embodiments, the catheter 20 may be steerable. For example, the catheter 20 may include one or more steering wires configured to steer the distal end 22 of the catheter 20 in one or more directions. In other embodiments, the catheter 20 may not be steerable. Instead, a guidewire may first be used to access the target site. Then the catheter 20 may be disposed over the guidewire, and advanced distally using the guidewire. In such cases, the catheter 20 may include a separate channel for accommodating the guidewire.

After the distal end 22 of the catheter 20 is desirably placed, the shaft 30 (shown in FIG. 1) is then advanced to push the embolic device 100 distally until a first distal portion of the embolic device 100 is outside the catheter 20 (FIG. 8A). The embolic device 100 has a straight profile when in room temperature residing inside the catheter 20. The straight profile is due to the embolic device 100 being in room temperature, and it is not due to any mechanical straightening imposed by the catheter 20. Accordingly, the embolic device 100 can be easier advanced distally. This feature also allows a longer embolic device 100 to be delivered if needed. As shown in the figure, the first portion of the elongated member 102 responds to body temperature by changing from its relatively straight shape to form a first part of the three-dimensional structure 112 when the first portion of the elongated member 102 is unconfined outside the catheter 20. In particular, the reversible Martensite segments (e.g., segments 300, 304, 410, 414, etc.) along the elongated member 102 change phase to become Austenite segments in response to body temperature. These Austenite segments have curvilinear profiles to provide the delivery shape for the portions of the elongated member 102 that has been deployed. The irreversible Martensite segments (e.g., segments 302, 412, etc.) along the elongated member 102 remains in the Martensite phase. These irreversible Martensite segments are softer compared to the reversible Martensite segments, and therefore they are easier to be bent in response to force. Accordingly, as the first part of the three-dimensional structure 112 is delivered into the aneurysm, the loops of the three-dimensional structure 112 are pressed towards the wall of the aneurysm, which imposes a force onto the irreversible Martensite segments. These segments bend in response to the force, thereby allowing the delivered first part of the three-dimensional structure 112 to better conform to the shape of the aneurysm 700.

In the illustrated example, the first part of the three-dimensional structure 112 has a shape that corresponds with an inner wall of the aneurysm. The first part of the three-dimensional structure 112, represented schematically by the dashed line in FIG. 8A, provides a frame defining the cavity 118 for accommodating subsequent portions of the embolic device 100 to be delivered. As shown in the figure, the first part of the three-dimensional structure 112 also provides a scaffolding across a neck 704 of an aneurysm 700, which assists in containing subsequent portion(s) of the elongated member 102 of the embolic device 100 to be delivered into the cavity 118.

Next, the shaft 30 may be advanced further to push a subsequent portion of the embolic device 100 out of the catheter 20 (FIG. 8B). As shown in the figure, the subsequent portion forms a second part of the three-dimensional structure 112 when the subsequent portion is unconfined outside the catheter 20. The second part of the three-dimensional structure 112 has a shape that allows it to fill at least some of the space in the cavity 118 defined by the first part of the three-dimensional structure 112. As shown in the figure, the scaffolding across the neck 704 of the aneurysm provided by the first part of the three-dimensional structure 112 prevents the second part of the three-dimensional structure 112 from escaping or falling out of the cavity 118 of the first part of the three-dimensional structure 112 and out of the aneurysm.

As similarly discussed with reference to the first part of the three-dimensional structure 112, for the second part of the three-dimensional structure 112, the reversible Martensite segments along the elongated member 102 change phase to become Austenite segments in response to body temperature. These Austenite segments have curvilinear profiles to provide the delivery shape for the portions of the elongated member 102 that has been deployed. On the other hand, the irreversible Martensite segments along the elongated member 102 remains in the Martensite phase. These irreversible Martensite segments are softer compared to the reversible Martensite segments, and therefore they are easier to be bent in response to force. Accordingly, as the second part of the three-dimensional structure 112 is delivered into the aneurysm, the loops of the three-dimensional structure 112 are pressed towards the wall of the aneurysm (or towards the first part of the three-dimensional structure 112), which imposes a force onto the irreversible Martensite segments. These segments bend in response to the force, thereby allowing the delivered second part of the three-dimensional structure 112 to better conform to the shape of the cavity to be filled.

In some embodiments, the distal end of the shaft 30 abuts against the proximal end of the elongated member 102, and is not mechanically attached to the proximal end of the elongated member 102. In such cases, the elongated member 102 becomes decoupled from the remaining part of the medical device 10 as soon as the proximal end of the elongated member 102 is pushed out of the catheter 20. In other embodiments, the distal end of the shaft 30 may be mechanically connected to the proximal end of the elongated member 102, such as via a mechanical connector that is operable to disengage the proximal end of the elongated member 102 from the shaft 30. In further embodiments, the distal end of the shaft 30 may be mechanically connected to the proximal end of the elongated member 102 via a disintegratable link, such as a link that can be disintegrated in response to application of a current. Mechanical connectors and disintegratable links are well known in the art, and therefore will not be described in further detail.

As illustrated in the above embodiments, the embolic device 100 is advantageous because the softer individual discrete irreversible Martensite segments provide some flexibility for the embolic device 100, thereby allowing the embolic device 100 to bend easily in response to force. While certain discrete parts (the irreversible Martensite segments) of the embolic device 100 can be more easily bent, a majority of other parts (i.e., the reversible Martensite segments) of the embolic device 100 remains relatively stiffer compared to the irreversible Martensite segments, thereby allowing the shape of most of the parts of the embolic device 100 to be maintained within the body cavity. In addition, the embolic device 100 is also advantageous because it has a delivery shape within the catheter 20 that is relatively straight compared to its deployed shape. This allows the embolic device 100 to be advanced distally relative to the catheter 20 easily without use of significant axial pushing force, and reduces the risk of the embolic device 100 buckling within the catheter 20.

In some embodiments, multiple embolic devices 100 may be provided with different respective lengths. In such cases, before one of the embolic devices 100 is selected for treating an aneurysm, a doctor may measure a size of the aneurysm to be treated. For example, the doctor may perform measurement using one or more images of the aneurysm to determine the size of the aneurysm. The size may be a cross-sectional dimension of the aneurysm, a cross-sectional area of the aneurysm, a volume of the aneurysm, etc. After a size of the aneurysm has been determined, one of the embolic devices 100 may then be selected based on the size of the aneurysm. For example, a longer embolic device 100 may be selected to occlude a larger aneurysm.

Figure 9:
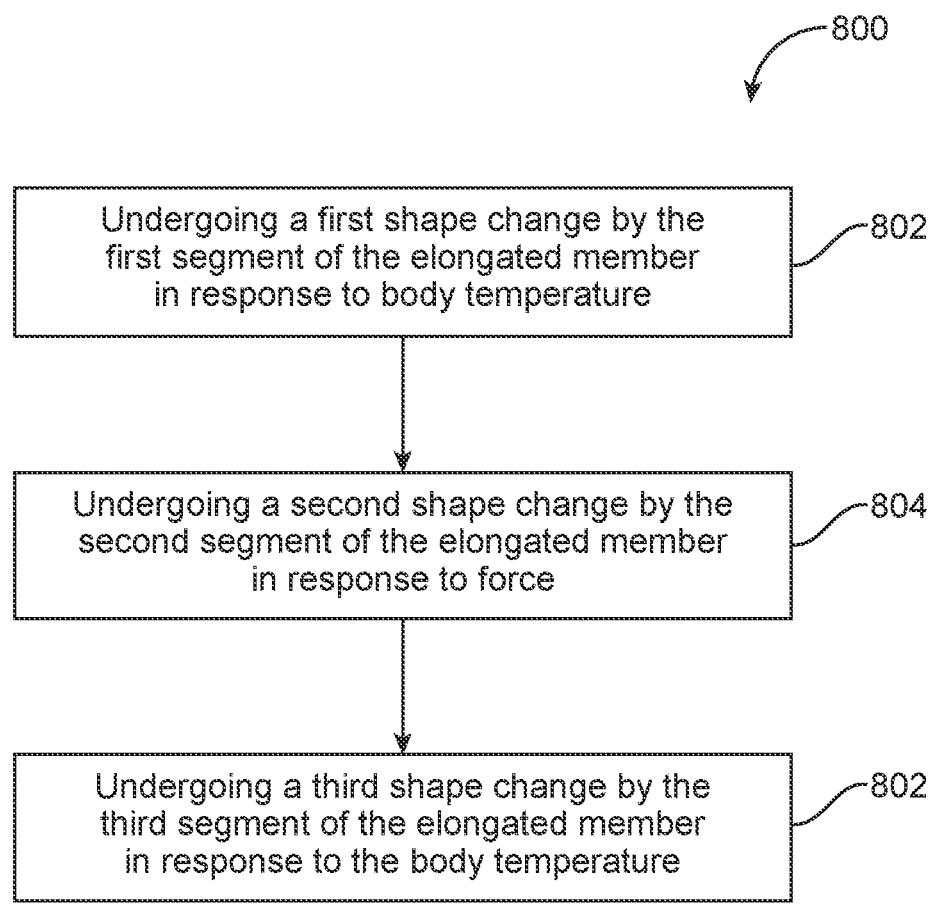
FIG. 9 illustrates a method of delivering an embolic device into an aneurysm.

FIG. 9 illustrates a method 800 of occluding a body lumen. The method 800 is performed by an embolic device having an elongated member, the elongated member comprising a first segment, a second segment, and a third segment, wherein the second segment is between the first segment and the third segment. The method 800 includes: undergoing a first shape change by the first segment of the elongated member in response to body temperature (item 802); undergoing a second shape change by the second segment of the elongated member in response to force (item 804); and undergoing a third shape change by the third segment of the elongated member in response to the body temperature (item 806).

In some embodiments, the embolic device in the method 800 may be the embolic device 100 described herein.

Optionally, in the method, the first segment is martensitic when the first segment is in the room temperature, and is austenitic when the first segment is in the body temperature; and wherein the second segment is martensitic when the second segment is in the room temperature, and is also martensitic when the second segment is in the body temperature.

Optionally, in the method, the first segment forms a first part of a loop, and the third segment forms a second part of the loop, in response to the body temperature.

Optionally, in the method, the first segment forms a first loop, and the third segment forms a second loop, in response to the body temperature.

Optionally, in the method, the first segment has a first length, the second segment has a second length, and the third segment has a third length; and wherein the second length of the second segment is shorter than the first length of the first segment, and is also shorter than the third length of the third segment.

Optionally, in the method, the second length of the second segment that is between the first segment and the third segment is less than 50% of the first length of the first segment, and is also less than 50% of the third length of the third segment.

Optionally, in the method, the elongated member has a distal end and a proximal end opposite from the distal end, and wherein the embolic device further comprises a fourth segment that includes the proximal end; and wherein the fourth segment is martensitic when in the room temperature, and is also martensitic when the fourth segment is the body temperature.

Optionally, in the method, the three-dimensional structure comprises a plurality of loops, and wherein the first segment, the second segment, and the third segment are parts of one of the loops.

Optionally, in the method, the elongated member further comprises a fourth segment, a fifth segment, and a sixth segment that are parts of another one of the loops; wherein the fifth segment is between the fourth segment and the sixth segment; wherein the fourth segment and the sixth segment are martensitic when the fourth segment and the sixth segment are in the room temperature, and are austenitic when the fourth segment and the sixth segment are in the body temperature; and wherein the fifth segment is martensitic when the fifth segment is in the room temperature, and is also martensitic when the fifth segment is in the body temperature.

The following items are exemplary features of embodiments described herein. Each item may be an embodiment itself or may be a part of an embodiment. One or more items described below may be combined with other item(s) in an embodiment.

Item 1: An embolic device for placement in a body lumen, includes: an elongated member having a linear configuration when in room temperature, the elongated member being configured to form a first three-dimensional structure in response to body temperature; wherein the elongated member comprises a first segment, a second segment, and a third segment, the second segment being located between the first segment and the third segment; wherein the first segment and the third segment are configured to change their respective shapes in response to the body temperature; and wherein the second segment that is located between the first segment and the third segment has a shape that is independent of the body temperature.

Item 2: The first segment is configured to form a first part of a loop, and the third segment is configured to form a second part of the loop in response to the body temperature.

Item 3: The first segment is configured to form a first loop, and the third segment is configured to form a second loop, in response to the body temperature.

Item 4: The first segment has a first length, the second segment has a second length, and the third segment has a third length; and wherein the second length of the second segment is shorter than the first length of the first segment, and is also shorter than the third length of the third segment.

Item 5: The second length of the second segment that is between the first segment and the third segment is less than 50% of the first length of the first segment, and is also less than 50% of the third length of the third segment.

Item 6: The elongated member has a distal end and a proximal end opposite from the distal end, and wherein the embolic device further comprises a fourth segment that includes the proximal end; and wherein the fourth segment is martensitic when the fourth segment is in the room temperature, and is also martensitic when the fourth segment is in the body temperature.

Item 7: The first segment is martensitic when the first segment is in the room temperature, and is austenitic when the first segment is in the body temperature.

Item 8: The second segment is martensitic when the second segment is the room temperature, and is martensitic when the second segment is in the body temperature.

Item 9: The three-dimensional structure comprises a plurality of loops, and wherein the first segment, the second segment, and the third segment are parts of one of the loops.

Item 10: The elongated member further comprises a fourth segment, a fifth segment, and a sixth segment that are parts of another one of the loops; wherein the fifth segment is between the fourth segment and the sixth segment; wherein the fourth segment and the sixth segment are configured to change their respective shapes in response to the body temperature; and wherein the fifth segment that is located between the fourth segment and the sixth segment has a shape that is independent of the body temperature.

Item 11: An embolic device for placement in a body lumen, includes: an elongated member having a linear configuration when in room temperature, the elongated member being configured to form a first three-dimensional structure in response to body temperature; wherein the elongated member comprises a first segment, a second segment, and a third segment, the second segment being located between the first segment and the third segment; wherein the first segment is martensitic when the first segment is in the room temperature, and is austenitic when the first segment is in the body temperature; and wherein the second segment is martensitic when the second segment is in the room temperature, and is also martensitic when the second segment is in the body temperature.

Item 12: The first segment is configured to form a first part of a loop, and the third segment is configured to form a second part of the loop, in response to the body temperature.

Item 13: The first segment is configured to form a first loop, and the third segment is configured to form a second loop, in response to the body temperature.

Item 14: The first segment has a first length, the second segment has a second length, and the third segment has a third length; and wherein the second length of the second segment is shorter than the first length of the first segment, and is also shorter than the third length of the third segment.

Item 15: The second length of the second segment that is between the first segment and the third segment is less than 50% of the first length of the first segment, and is also less than 50% of the third length of the third segment.

Item 16: The elongated member has a distal end and a proximal end opposite from the distal end, and wherein the embolic device further comprises a fourth segment that includes the proximal end; and wherein the fourth segment is martensitic when in the room temperature, and is also martensitic when the fourth segment is the body temperature.

Item 17: The three-dimensional structure comprises a plurality of loops, and wherein the first segment, the second segment, and the third segment are parts of one of the loops.

Item 18: The elongated member further comprises a fourth segment, a fifth segment, and a sixth segment that are parts of another one of the loops; wherein the fifth segment is between the fourth segment and the sixth segment; wherein the fourth segment and the sixth segment are martensitic when the fourth segment and the sixth segment are in the room temperature, and are austenitic when the fourth segment and the sixth segment are in the body temperature; and wherein the fifth segment is martensitic when the fifth segment is in the room temperature, and is also martensitic when the fifth segment is in the body temperature.

Item 19: A method of occluding a body lumen performed by an embolic device having an elongated member, the elongated member comprising a first segment, a second segment, and a third segment, wherein the second segment is between the first segment and the third segment, includes: undergoing a first shape change by the first segment of the elongated member in response to body temperature; undergoing a second shape change by the second segment of the elongated member in response to force; and undergoing a third shape change by the third segment of the elongated member in response to the body temperature.

Item 20: The first segment is martensitic when the first segment is in the room temperature, and is austenitic when the first segment is in the body temperature; and wherein the second segment is martensitic when the second segment is in the room temperature, and is also martensitic when the second segment is in the body temperature.

Item 21: The first segment forms a first part of a loop, and the third segment forms a second part of the loop, in response to the body temperature.

Item 22: The first segment forms a first loop, and the third segment forms a second loop, in response to the body temperature.

Item 23: The first segment has a first length, the second segment has a second length, and the third segment has a third length; and wherein the second length of the second segment is shorter than the first length of the first segment, and is also shorter than the third length of the third segment.

Item 24: The second length of the second segment that is between the first segment and the third segment is less than 50% of the first length of the first segment, and is also less than 50% of the third length of the third segment.

Item 25: The elongated member has a distal end and a proximal end opposite from the distal end, and wherein the embolic device further comprises a fourth segment that includes the proximal end; and wherein the fourth segment is martensitic when in the room temperature, and is also martensitic when the fourth segment is the body temperature.

Item 26: The three-dimensional structure comprises a plurality of loops, and wherein the first segment, the second segment, and the third segment are parts of one of the loops.

Item 27: The elongated member further comprises a fourth segment, a fifth segment, and a sixth segment that are parts of another one of the loops; wherein the fifth segment is between the fourth segment and the sixth segment; wherein the fourth segment and the sixth segment are martensitic when the fourth segment and the sixth segment are in the room temperature, and are austenitic when the fourth segment and the sixth segment are in the body temperature; and wherein the fifth segment is martensitic when the fifth segment is in the room temperature, and is also martensitic when the fifth segment is in the body temperature.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An embolic device for placement in a body lumen, the embolic device comprising:
    an elongated member having a linear configuration when at room temperature, the elongated member being configured to form a first three-dimensional structure in response to body temperature;
    wherein the elongated member comprises a first segment, a second segment, and a third segment, the second segment being located between the first segment and the third segment;
    wherein the first segment and the third segment are configured to change their respective shapes in response to the body temperature;
    wherein the second segment that is located between the first segment and the third segment has a shape that is independent of the body temperature;
    wherein the first segment is martensitic when the first segment is at the room temperature, and is austenitic when the first segment is at the body temperature; and
    wherein the second segment that is between the first and third segments is softer than the first and third segments.

2. The embolic device of claim 1, wherein the first segment is configured to form a first part of a loop, and the third segment is configured to form a second part of the loop in response to the body temperature.

3. The embolic device of claim 1, wherein the first segment is configured to form a first loop, and the third segment is configured to form a second loop, in response to the body temperature.

4. The embolic device of claim 1,
    wherein the elongated member has a distal end and a proximal end opposite from the distal end, and wherein the embolic device further comprises a fourth segment that includes the proximal end; and
    wherein the fourth segment is martensitic when the fourth segment is at the room temperature, and is also martensitic when the fourth segment is at the body temperature.

5. The embolic device of claim 1, wherein the second segment is martensitic when the second segment is the room temperature, and is martensitic when the second segment is at the body temperature, and wherein the second segment comprises an irreversible martensitic segment.

6. The embolic device of claim 1, wherein the three-dimensional structure comprises a plurality of loops, and wherein the first segment, the second segment, and the third segment are parts of one of the loops.

7. The embolic device of claim 6, wherein the elongated member further comprises a fourth segment, a fifth segment, and a sixth segment that are parts of another one of the loops;
    wherein the fifth segment is between the fourth segment and the sixth segment;
    wherein the fourth segment and the sixth segment are configured to change their respective shapes in response to the body temperature; and
    wherein the fifth segment that is located between the fourth segment and the sixth segment has a shape that is independent of the body temperature.

8. An embolic device for placement in a body lumen, the embolic device comprising:
    an elongated member having a linear configuration when in room temperature, the elongated member being configured to form a first three-dimensional structure in response to body temperature;
    wherein the elongated member comprises a first segment, a second segment, and a third segment, the second segment being located between the first segment and the third segment;
    wherein the first segment is martensitic when the first segment is at the room temperature, and is austenitic when the first segment is at the body temperature; and
    wherein the second segment is martensitic when the second segment is at the room temperature, and is also martensitic when the second segment is at the body temperature, and wherein the second segment comprises an irreversible martensitic segment.

9. The embolic device of claim 8, wherein the first segment is configured to form a first part of a loop, and the third segment is configured to form a second part of the loop, in response to the body temperature.

10. The embolic device of claim 8, wherein the first segment is configured to form a first loop, and the third segment is configured to form a second loop, in response to the body temperature.

11. The embolic device of claim 8,
wherein the second segment extends from the first segment to the third segment, wherein the first segment has a first length, the second segment has a second length that is an entire length of the second segment, and the third segment has a third length; and
wherein the second length of the second segment is shorter than the first length of the first segment, and is also shorter than the third length of the third segment.

12. The embolic device of claim 11, wherein the second length of the second segment that is between the first segment and the third segment is less than 50% of the first length of the first segment, and is also less than 50% of the third length of the third segment.

13. The embolic device of claim 8,
wherein the elongated member has a distal end and a proximal end opposite from the distal end, and wherein the embolic device further comprises a fourth segment that includes the proximal end; and
wherein the fourth segment is martensitic when at the room temperature, and is also martensitic when the fourth segment is the body temperature.

14. The embolic device of claim 8, wherein the three-dimensional structure comprises a plurality of loops, and wherein the first segment, the second segment, and the third segment are parts of one of the loops.

15. The embolic device of claim 14, wherein the elongated member further comprises a fourth segment, a fifth segment, and a sixth segment that are parts of another one of the loops;
wherein the fifth segment is between the fourth segment and the sixth segment;
wherein the fourth segment and the sixth segment are martensitic when the fourth segment and the sixth segment are at the room temperature, and are austenitic when the fourth segment and the sixth segment are at the body temperature; and
wherein the fifth segment is martensitic when the fifth segment is at the room temperature, and is also martensitic when the fifth segment is at the body temperature.

16. A method of occluding a body lumen performed by an embolic device having an elongated member, the elongated member comprising a first segment, a second segment, and a third segment, wherein the second segment is between the first segment and the third segment, the method comprising:
undergoing a first shape change by the first segment of the elongated member in response to body temperature;
undergoing a second shape change by the second segment of the elongated member in response to force, wherein the second segment comprises an irreversible martensitic segment; and
undergoing a third shape change by the third segment of the elongated member in response to the body temperature;
wherein the second segment underwent the second shape change in response to force after the first segment is subject to the body temperature, and before the third segment is subject to the body temperature;
wherein the first segment is martensitic when the first segment is at the room temperature, and is austenitic when the first segment is at the body temperature; and
wherein the second segment is martensitic when the second segment is at the room temperature, and is also martensitic when the second segment is at the body temperature.

* * * * *